(12) United States Patent
Gattrell

(10) Patent No.: US 7,390,838 B2
(45) Date of Patent: Jun. 24, 2008

(54) DEPIGMENTING AGENTS

(75) Inventor: William Thomas Gattrell, Bicester (GB)

(73) Assignee: Pfizer Inc., New York, NY (US)

( * ) Notice: Subject to any disclaimer, the term of this patent is extended or adjusted under 35 U.S.C. 154(b) by 635 days.

(21) Appl. No.: 10/848,656

(22) Filed: May 19, 2004

(65) Prior Publication Data

US 2004/0235963 A1 Nov. 25, 2004

Related U.S. Application Data

(60) Provisional application No. 60/472,055, filed on May 20, 2003.

(51) Int. Cl.
*A61K 31/045* (2006.01)
*A61K 31/05* (2006.01)

(52) U.S. Cl. .................. 514/729; 514/730; 514/731
(58) Field of Classification Search ................ 514/719, 514/729, 730, 731
See application file for complete search history.

(56) References Cited

U.S. PATENT DOCUMENTS 6,132,740 A * 10/2000 Hu .......................... 424/401
2004/0235963 A1* 11/2004 Gattrell ...................... 514/719

OTHER PUBLICATIONS

U.S. Appl. No. 10/766,078, Gattrell et al.

* cited by examiner

*Primary Examiner*—Alton Pryor
(74) *Attorney, Agent, or Firm*—Gregg C. Benson

(57) ABSTRACT

The present invention is directed to crystalline forms of anhydrous 4-cyclopentyl resorcinol, the Form A and C polymorphs, formulations containing at least one of these crystalline forms and their use to lighten skin.

5 Claims, 4 Drawing Sheets

DEPIGMENTING AGENTS

CROSS-REFERENCE TO RELATED APPLICATIONS

This application claims priority from U.S. Provisional Patent Application No. 60/472,055 filed May 20, 2003.

FIELD OF THE INVENTION

The present invention is directed to crystalline forms of anhydrous 4-cyclopentyl resorcinol.

BACKGROUND OF THE INVENTION

In humans, skin color arises from a complex series of cellular processes that are carried out within a group of cells known as melanocytes. Melanocytes are located in the lower part of the epidermis and their function is to synthesize a pigment, melanin, which protects the body from the damaging effects of ultraviolet radiation.

The mechanism by which skin pigmentation is formed, melanogenesis, involves the following main steps: Tyrosine→L-Dopa→Dopaquinone Dopachrome→Melanin. The first two reactions in this series are catalyzed by the enzyme, tyrosinase. The activity of tyrosinase is promoted by the action of α-melanocyte stimulating hormone and UV rays.

Typically, melanogenesis leads to a darker skin tone (i.e. a tan). However, melanogenesis can lead to undesirable pigmentation patterns as well. Examples of such undesirable pigmentation include age spots, liver spots, melasma, hyperpigmentation, etc. This has lead to research to find compounds that will inhibit melanogenesis. One of the targets of this research is tyrosinase, the enzyme which catalyses the initial steps in the generation of melanin.

U.S. Pat. No. 6,132,740 discloses a class of tyrosinase inhibitors. These compounds are 4-cycloalkyl resorcinols. One compound disclosed in the '740 patent is 4-cyclopentyl resorcinol. Example 2 of the '740 patent illustrates the preparation of amorphous 4-cyclopentyl resorcinol. While this compound is a potent tyrosinase inhibitor, it may not be readily produced in the quantities required to support clinical development. The synthesis of example 2 generates substantial quantities of various positional isomers of 4-cyclopentyl resorcinol. Examples of such isomers include 2-cyclopentyl resorcinol, 4,6-dicyclopentyl resorcinol, 2,4-dicyclopentyl-resorcinol, etc. It is difficult to separate the 4-cyclopentyl resorcinol from its positional isomers.

Crystalline forms of 4-cyclopentyl resorcinol may be readily separated from the positional isomers that are generated in its synthesis. These crystalline forms of anhydrous 4-cyclopentyl resorcinol are typically more amendable to handling and formulating at clinical or industrial scale than are amorphous forms. Other advantages of crystalline forms of 4-cyclopentyl resorcinol will be readily apparent to those skilled in the art.

SUMMARY OF THE INVENTION

In accordance with the present invention, new crystalline forms of anhydrous 4-cyclopentyl resorcinol have been discovered. Two different forms have been discovered to date. These crystalline forms are referred to as Forms A and C. The structure of 4-cyclopentyl resorcinol is depicted by Formula I:

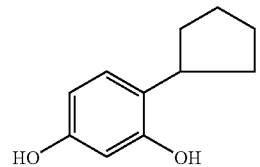

Formula I

The structure of a single crystal of the Form A polymorph has been determined. Based upon the structure of this single crystal, a powder X-ray diffraction pattern was calculated for the Form A polymorph. The IR spectra of the Form A polymorph was also determined. All of these values are reported infra.

The structure of a single crystal of the Form C polymorph was determined. Based upon the structure of this single crystal, a powder X-ray diffraction pattern was calculated for the Form C polymorph. The IR spectra of this polymorph was determined. All of these values are reported infra.

The crystalline forms of anhydrous 4-cyclopentyl resorcinol may be used to lighten skin (i.e. as a depigmentation agent). In a more specific embodiment, at least one of the crystalline forms is incorporated into a topical dosage form, which the patient may apply directly to the area of the skin requiring lightening.

In a further embodiment, the invention is directed to an article of manufacture containing at least one of these crystalline forms, packaged for retail distribution, in association with instructions advising the consumer how to use the product to lighten skin.

DETAILED DESCRIPTION OF THE INVENTION

A) Background

Compounds having identical chemical structures may exist in different physical forms. For example, these compounds may exist as solids, liquids, or gases. Solid forms may be amorphous or may exist as distinct crystalline forms. Different crystalline forms often have different physical properties (i.e. bioavailability, solubility, melting points, etc).

These different crystalline forms are called polymorphs. One method of determining the structure of a polymorph is single crystal X-ray analysis. In this analysis the crystalline state of a compound is described by several crystallographic parameters including unit cell dimensions, space group, and atomic position of all atoms in the compound relative to the origin of its unit cell.

Using this technique, it has been discovered that there are two polymorphs of anhydrous 4-cyclopentyl resorcinol. A comparison of the unit cell dimensions and space groups of these two crystalline states are given in Tables I and IV below. A more detailed discussion of single crystal X-ray analysis may be found in International Tables for X-ray Crystallography, Vol. IV, pp. 55, 99, 149 Birmingham: Kynoch Press, 1974, G. M. Sheldrick, SHELXTL. User Manual, Nicolet Instrument Co., 1981 and in Crystal Structure Analysis by Glusker, and Trueblood, 2nd ed.; Oxford University press: New York, 1985.

Single crystal X-ray analysis is limited to, as the name implies, the one crystal placed in the X-ray beam. Techniques have also been developed to collect crystallographic data on a large group of crystals, which is commonly referred to as powder X-ray diffraction.

The data generated in determining the structure of a single crystal allows one skilled in the art to calculate a powder X-ray diffraction pattern. This conversion is possible because the single crystal experiment routinely determines the unit cell dimensions, space group, and atomic positions. These parameters provide a basis to calculate the powder pattern for a particular polymorph. This may be accomplished with the aid of computer software such as SHELXTL Plus (trademark) computer program, Reference Manual by Siemens Analytical X-ray Instrument, Chapter 10, p. 179-181, 1990, or alternatively by PowderCell by W. Kraus and G. Nolze, Berlin, Germany, 1999.

Figure 1:
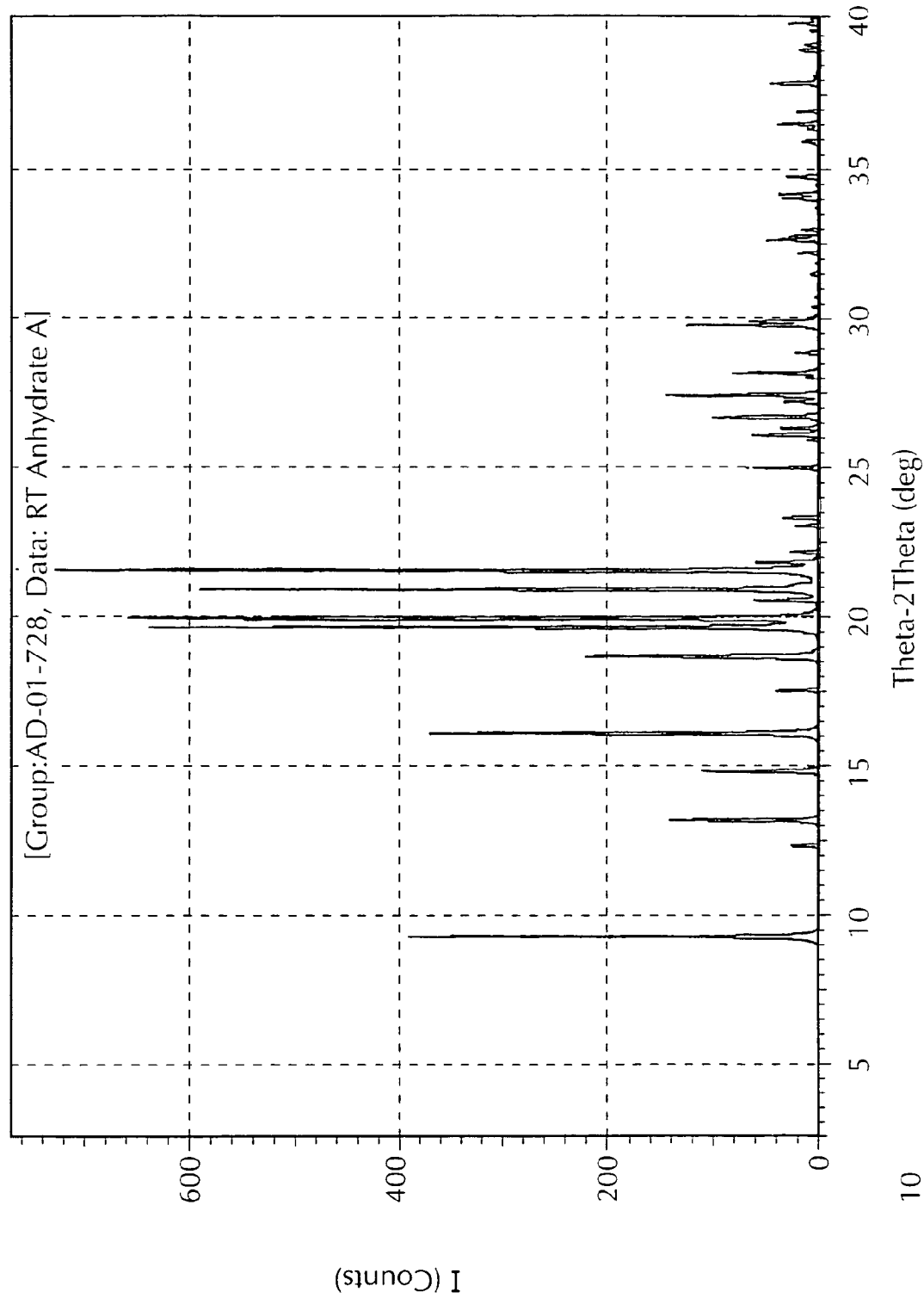
FIG. 1 depicts a calculated X-ray diffraction pattern for the Form A polymorph.
Figure 2:
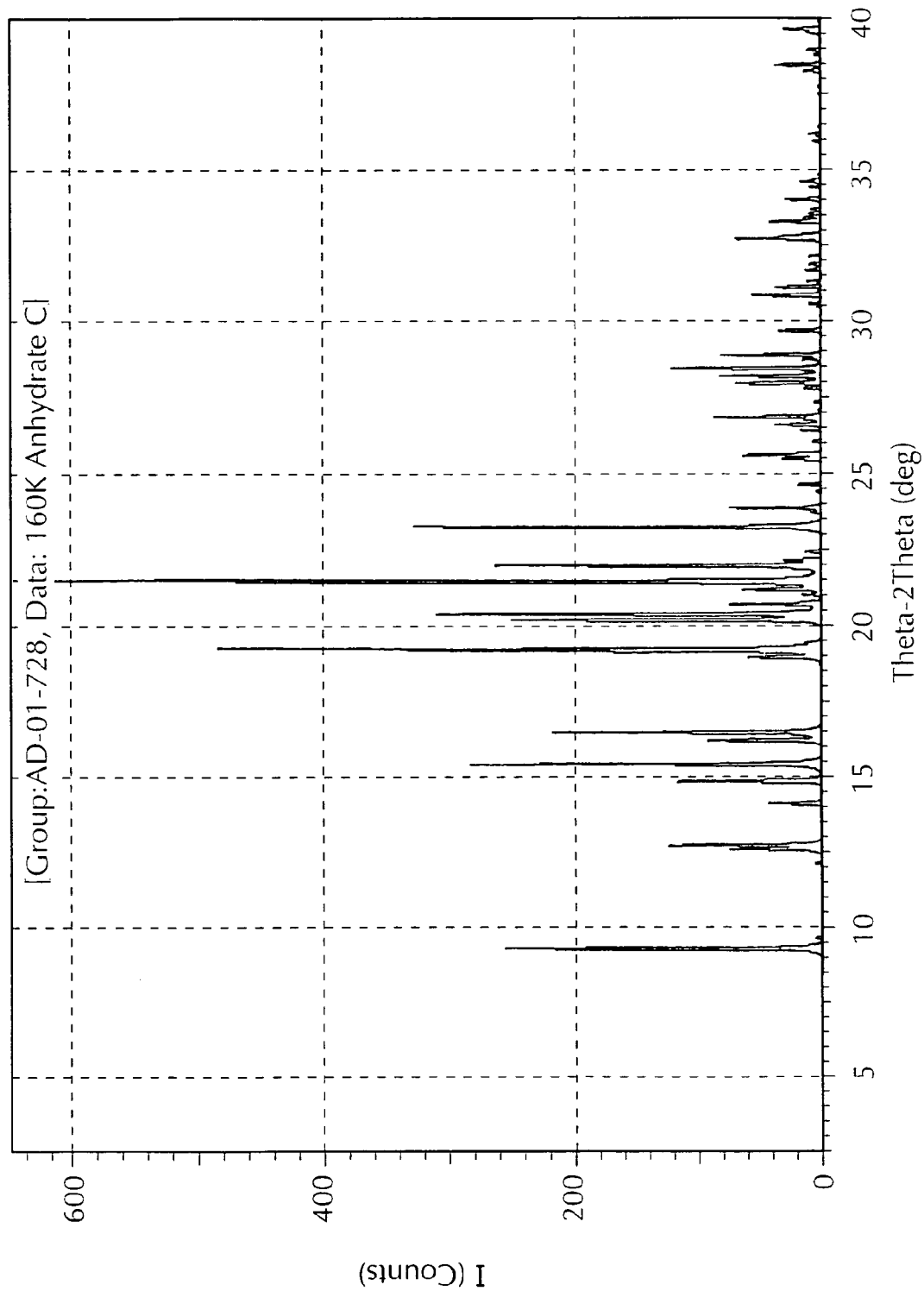
FIG. 2 depicts a calculated X-ray diffraction pattern for the Form C polymorph.

This technique of translating single crystal data into a powder diffraction graph has been used to produce a graph of the X-ray diffraction patterns for both the Form A and Form C polymorphs. The results of these calculations are depicted in FIGS. 1 and 2 infra.

B) Methods of Characterization

The single crystal X-ray analysis and the calculated X-ray diffraction patterns were determined as described below:

i) Single Crystal X-ray Analysis

A single crystal of the relevant polymorph (i.e. A or C) was mounted in a random orientation. Preliminary examination and data collection were performed with Mo $K_\alpha$ radiation on a Bruker SAMRT IK CCD diffractometer, available from Bruker AXS, Inc., Madison, Wis. Cell constants and an orientation matrix for data collection were obtained from least-squares refinement using the setting angles of 6145 reflections in the range $3<\theta<28°$. The structure was solved by direct methods. The structure was refined by full-matrix least-squares on $F^2$. The crystal structure of the Form A polymorph was determined at 293 K, solved in space group $P2_1/c$ and refined to a final R of 0.10 ($F^2>2\sigma$). The crystal structure of the Form C polymorph was determined at 160 K, solved in space group P-1 and refined to a final R of 0.08 ($F^2>2\sigma$).

ii) Calculated X ray Diffraction Pattern

Calculated XRPD patterns were generated using PowderCell v. 2.3 from the single crystal atomic co-ordinates, unit cell parameters, and symmetry. The calculated pattern of the Form A polymorph was generated from single crystal data collected at 293 K (20° C.), whereas the Form C data was collected at 160 K (–113° C.). The XRPD patterns were generated for Cu radiation with Bragg-Bretano geometry, and a 0.02°2θ step size. A pseudo-Voigt$^2$ profile with FWHM=f (u,v,w), where u=0, v=0, and w=0.005 was employed. No scaling factor was used.

Experimental x-ray powder diffraction (XRPD) is another means for determining whether a particular crystalline form of anhydrous 4-cyclopentyl resorcinol is the Form A or Form C polymorph. A calculated XRPD pattern exhibits the peaks, which are likely to appear in an experimental XPRD pattern. While one skilled in the art will realize that the relative intensities of peaks present in an actual experimental XPRD pattern may vary due to the preferred orientation of the particular crystals, the XPRD experiment may be carried out using techniques to minimize these effects. Such techniques include, for example, grinding of the sample before analysis, spinning or rocking the sample during analysis, or utilization of a diffractometer equipped with an area detector.

Thus, merely because an experimental XPRD is not identical to the calculated XPRD's depicted in FIG. 1 or 2, does not mean that a crystal is not the Form A or Form C polymorph. As will be discussed infra, the presence of selected characteristic peaks, identified from the calculated patterns, may be used to determine whether a crystalline form of anhydrous 4-cyclopentylresorcinol is the Form A or Form C polymorph.

iii) Infrared Absorption Spectrum

IR Spectra were recorded as KBr discs on a Nicloet 210 FT Spectrometer.

iv) Melting Point

Figure 4:
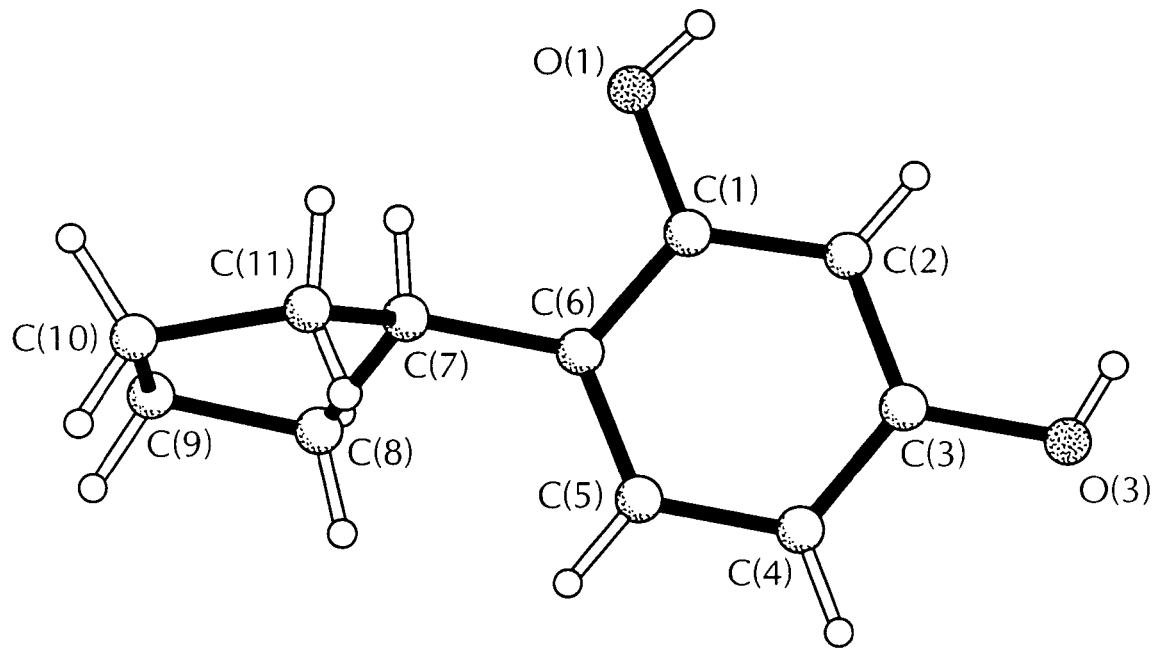
FIGS. 4A and 4B is an Ortep representation of the structure of a single crystal of the Form A polymorph.
Figure 4:
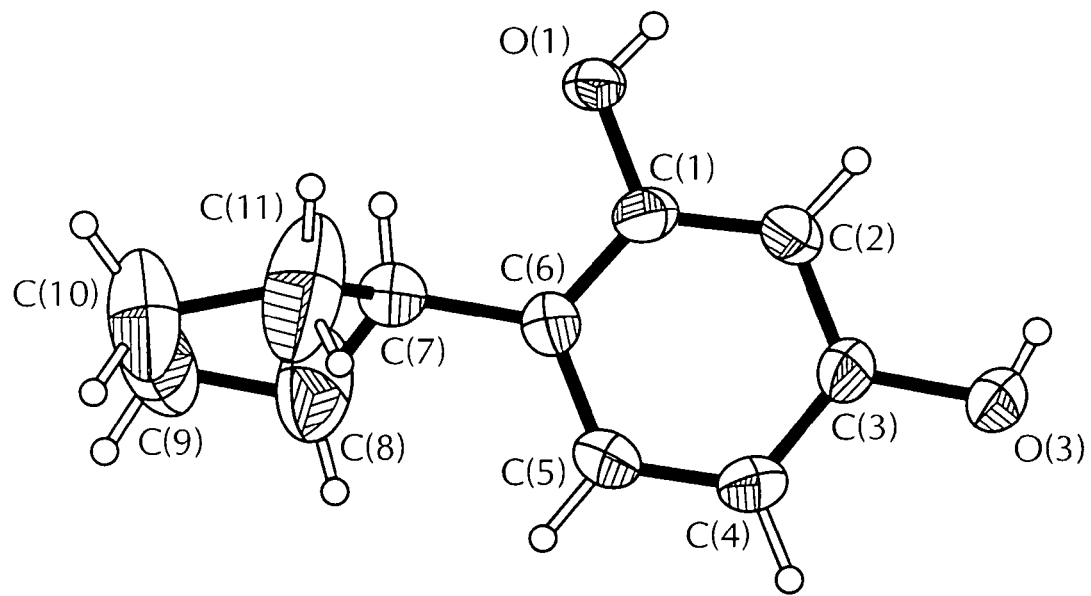

All melting points described herein were determined on a Kofler hot stage (observation under polarizing filter) and are uncorrected.

v) Ortep→The crystallographic drawing depicted in FIG. 4 was obtained using the program ORTEP.

A number of methodologies may be used in determining if a crystalline form of anhydrous 4-cyclopentyl resorcinol is the Form A or Form C polymorph. The Form A and Form C polymorphs may be identified on the basis of their single crystal structures. The calculated patterns provide an alternative means of characterizing the particular crystalline form, especially when used in conjunction with experimental XPRD. Other alternative means will be readily apparent to one skilled in the art based upon the disclosure contained within this application.

C) Form A Polymorph

One of the crystalline forms of anhydrous 4-cyclopentyl resorcinol is the Form A polymorph. It has a melting point of 65-66.5° C. The structure of the Form A polymorph was determined by single crystal X-ray analysis at 293 K. The unit cell parameters are shown below in Table I. Table II depicts the atomic coordinates and isotropic displacement parameters. Table III depicts hydrogen coordinates and isotropic displacement parameters.

TABLE I

| Space Group and Unit Cell Parameters | |
|---|---|
| Form | A |
| Crystal system | monoclinic |
| Space group | $P2_1/c$ |
| Cell Dimensions | |
| a(Å) | 9.582 ± 0.001 |
| b(Å) | 9.379 ± 0.001 |
| c(Å) | 11.076 ± 0.001 |
| β(°) | 97.405 ± 0.002 |
| Volume(Å$^3$) | 987 ± 1 |
| Z(Molecules/unit cell) | 4 |
| Density (g/cm$^3$) | 1.20 g/cm$^3$ |

TABLE II

Atomic coordinates and equivalent isotropic displacement parameters (Å$^2$) for Anhydrate A

| | x | y | z |
|---|---|---|---|
| C(1) | 0.8501(4) | 0.4729(4) | 0.7216(3) |
| C(2) | 0.9034(4) | 0.3450(4) | 0.6856(3) |

TABLE II-continued

Atomic coordinates and equivalent isotropic
displacement parameters (Å²) for Anhydrate A

| | x | y | z |
|---|---|---|---|
| C(3) | 0.8890(5) | 0.3112(4) | 0.5632(4) |
| C(4) | 0.8231(6) | 0.4036(5) | 0.4786(4) |
| C(5) | 0.7719(6) | 0.5307(5) | 0.5169(4) |
| C(6) | 0.7828(4) | 0.5694(4) | 0.6385(4) |
| C(7) | 0.7194(5) | 0.7072(5) | 0.6799(4) |
| C(8) | 0.7347(7) | 0.8401(5) | 0.6075(6) |
| C(9) | 0.6309(6) | 0.9415(6) | 0.6462(6) |
| C(10) | 0.5124(7) | 0.8518(6) | 0.6792(7) |
| C(11) | 0.5644(7) | 0.7008(6) | 0.6833(8) |
| O(1) | 0.8648(3) | 0.5098(3) | 0.8432(2) |
| O(3) | 0.9408(4) | 0.1855(3) | 0.5217(3) |

TABLE III*

Hydrogen coordinates and isotropic displacement parameters (Å²)

| | x | y | z |
|---|---|---|---|
| H(2) | 0.9484 | 0.2824 | 0.7431 |
| H(4) | 0.8129 | 0.3808 | 0.3962 |
| H(5) | 0.7282 | 0.5931 | 0.4587 |
| H(7) | 0.7636 | 0.7259 | 0.7632 |
| H(8A) | 0.8294 | 0.8781 | 0.6245 |
| H(8B) | 0.7150 | 0.8208 | 0.5210 |
| H(9A) | 0.5979 | 1.0063 | 0.5805 |
| H(9B) | 0.6723 | 0.9967 | 0.7158 |
| H(10A) | 0.4303 | 0.8619 | 0.6188 |
| H(10B) | 0.4873 | 0.8800 | 0.7579 |
| H(11A) | 0.5441 | 0.6543 | 0.7573 |
| H(11B) | 0.5189 | 0.6477 | 0.6140 |
| H(1) | 0.8830 | 0.4383 | 0.8850 |
| H(3) | 0.9970 | 0.1502 | 0.5756 |

*Hydrogen atoms were included in the refinement but restrained to ride on the atom to which they are bonded.

The data generated by single crystal X-ray analysis allowed the calculation of an X-ray diffraction pattern (i.e. a calculated XPRD). The results of these calculations are depicted in FIG. 1. These calculations allowed the determination of characteristic peaks associated with the Form A polymorph. A characteristic peak is a peak, which does not overlap with any peak appearing in a X-ray diffraction pattern for the Form C polymorph or the Form I polymorph of the monohydrate of 4-cyclopentyl resorcinol (see U.S. Patent application Ser. No. 60/446,665, which is hereby incorporated by reference, for a complete description of this crystalline form).

The characteristic peaks of the Form A polymorph, expressed in degrees 2θ (approximate) are located at 13.3, 18.7, 19.7, 27.4, and 29.8. Any reference in this application, including the claims, to an approximate 2θ value refers to the stated 2θ value ±0.2°2θ. The presence of at least one of these characteristic peaks in a crystalline sample of anhydrous 4-cyclopentyl resorcinol, submitted to experimental X-ray diffraction at a temperature of 293K (20° C.), is sufficient to confirm that the sample is the Form A polymorph. In a further embodiment, the presence of at least two, three, four, or five of these peaks in a crystalline sample of anhydrous 4-cyclopentyl resorcinol, submitted to experimental X-ray diffraction, is sufficient to confirm that the sample is the Form A polymorph. In a more specific embodiment, the presence of characteristic peaks at 18.7 and 19.7 degrees 2θ (approximate) is sufficient to confirm that the crystalline substance is the Form A polymorph. Any experimental X-ray diffraction should be carried out as described above, to minimize the impact that preferred orientation may have on the pattern generated.

A review of FIG. 1 identifies that additional peaks may be present in any sample of the Form A polymorph. A listing of the peaks identified in the calculated pattern, including the characteristic peaks identified above, is listed below in Table IV. The data presented in Table IV should be used to assist in the interpretation of an experimental X-ray diffraction pattern. The data should not be used conclude that a crystalline sample of anhydrous 4-cyclopentyl resorcinol is not the Form A polymorph due to the absence of one, or more, selected peaks.

TABLE IV

| 2θ[1] |
|---|
| 9.3 |
| 13.3* |
| 14.9 |
| 16.2 |
| 18.7* |
| 19.7* |
| 20.0 |
| 21.0 |
| 21.6 |
| 26.1 |
| 26.7 |
| 27.4* |
| 28.2 |
| 29.8* |

*Characteristic peak
[1]All stated 2θ values are approximate

Figure 3:
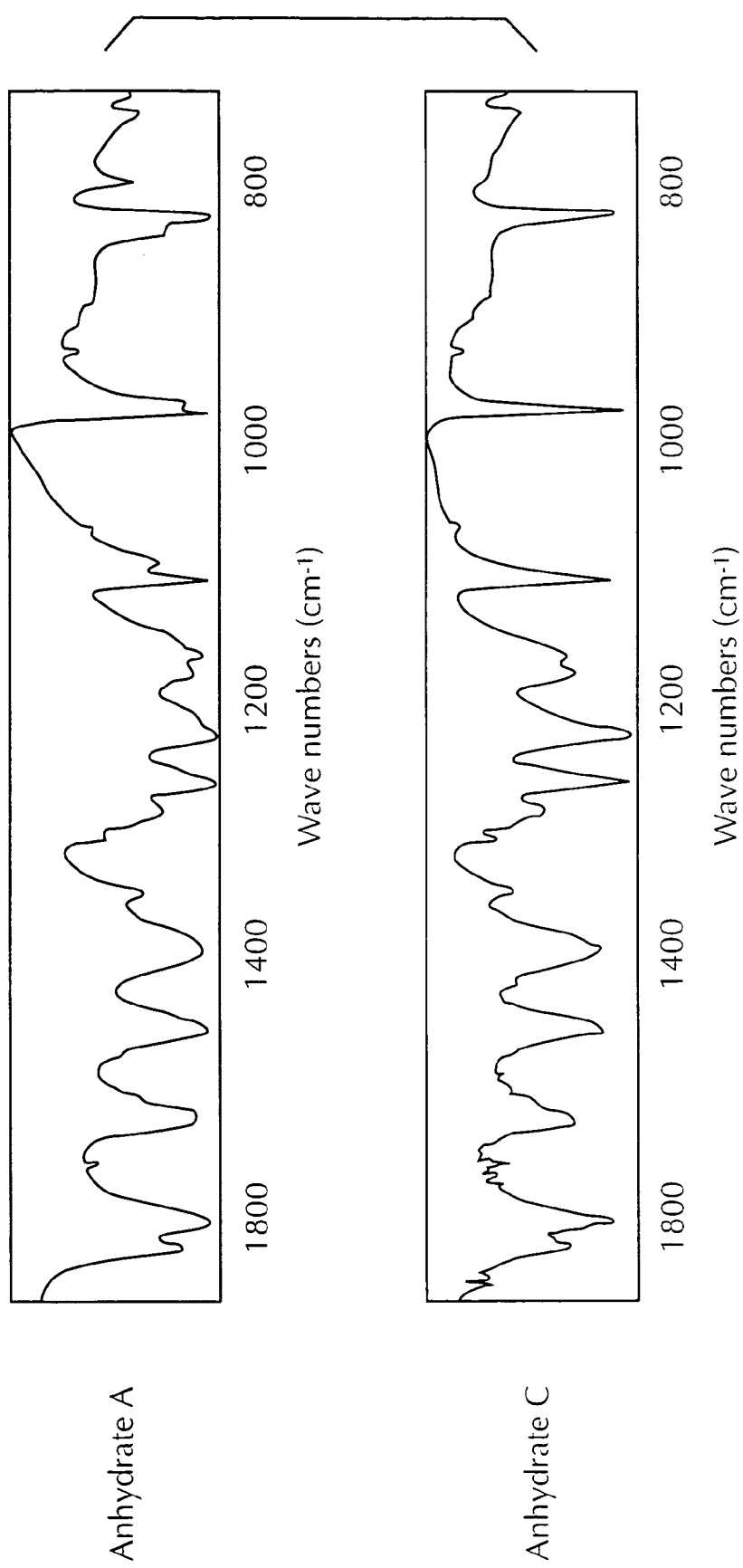
FIG. 3 depicts the IR spectra of the Forms A and C polymorphs.

The Form A polymorph has also been examined by infrared absorption spectroscopy. The IR spectra for this polymorph is shown in FIG. 3. Selected IR bands were identified that are unique to the Form A polymorph (i.e. are not present in the Form C polymorph). Form A exhibits the following unique absorption bands ($\upsilon_{max}$/cm$^{-1}$): 1094.7 m, 971.1 s, 930.4 w, 838.3 m, 799.8 w, and 748.1 w.

D) Form C Polymorph

The Form C polymorph is the second crystalline form of anhydrous 4-cyclopentyl resorcinol identified to date. It has a melting point of 63.2-66.5° C. It's structure has been determined by single crystal X-ray analysis at 160 K. The unit cell parameters are shown below in Table V. Table VI depicts the atomic coordinates and isotropic displacement parameters. Table VII depicts the hydrogen atom coordinates and isotropic displacement parameters.

TABLE V

Space Group and Unit Cell Parameters for Form C Polymorph

| Form | C |
|---|---|
| Crystal system | triclinic |
| Space group | P-1 |
| Cell Dimensions | |
| a(Å) | 9.180 ± 0.002 |
| b(Å) | 9.534 ± 0.002 |
| c(Å) | 10.831 ± 0.002 |
| α(°) | 87.493(3) |
| β(°) | 89.029(3) |
| γ(°) | 84.045(3) |
| Volume(Å³) | 942 ± 1 |
| Z(Molecules/unit cell) | 4 |
| Density (g/cm³) | 1.26 g/cm³ |

TABLE VI

Atomic coordinates and equivalent isotropic displacement parameters (A2)

| | x | y | z |
|---|---|---|---|
| C(1A) | 0.5108(5) | 0.6457(5) | 0.7321(4) |
| C(2A) | 0.6455(5) | 0.5876(5) | 0.6880(4) |
| C(3A) | 0.6755(5) | 0.5978(5) | 0.5626(4) |
| C(4A) | 0.5735(5) | 0.6651(5) | 0.4826(4) |
| C(5A) | 0.4397(5) | 0.7237(5) | 0.5293(4) |
| C(6A) | 0.4040(5) | 0.7146(5) | 0.6542(4) |
| C(7A) | 0.2601(5) | 0.7807(5) | 0.7084(5) |
| C(8A) | 0.1425(5) | 0.8308(5) | 0.6126(5) |
| C(9A) | 0.1676(6) | 0.9858(6) | 0.5760(5) |
| C(10A) | 0.2841(6) | 1.0260(5) | 0.6640(5) |
| C(11A) | 0.2823(5) | 0.9183(5) | 0.7715(5) |
| O(1A) | 0.4758(4) | 0.6342(4) | 0.8560(3) |
| O(3A) | 0.8066(4) | 0.5400(4) | 0.5137(3) |
| C(1B) | 1.0336(5) | 0.3447(5) | 0.7696(4) |
| C(2B) | 1.1549(5) | 0.4041(5) | 0.8104(4) |
| C(3B) | 1.1893(5) | 0.3913(5) | 0.9340(4) |
| C(4B) | 1.1038(6) | 0.3208(5) | 1.0169(4) |
| C(5B) | 0.9843(6) | 0.2623(5) | 0.9738(4) |
| C(6B) | 0.9443(5) | 0.2712(5) | 0.8494(4) |
| C(7B) | 0.8151(5) | 0.2022(6) | 0.8059(5) |
| C(8B) | 0.8300(6) | 0.0412(6) | 0.8241(6) |
| C(9B) | 0.6755(6) | −0.0007(6) | 0.8190(7) |
| C(10B) | 0.5754(6) | 0.1277(6) | 0.8506(6) |
| C(11B) | 0.6695(6) | 0.2437(6) | 0.8725(5) |
| O(1B) | 0.9984(3) | 0.3561(4) | 0.6457(3) |
| O(3B) | 1.3080(4) | 0.4487(4) | 0.9803(3) |

TABLE VII*

Hydrogen coordinates and isotropic displacement parameters ($Å^2$)

| | x | y | z |
|---|---|---|---|
| H(2A) | 0.7162 | 0.5415 | 0.7432 |
| H(4A) | 0.5942 | 0.6714 | 0.3964 |
| H(5A) | 0.3705 | 0.7715 | 0.4738 |
| H(7A) | 0.2205 | 0.7126 | 0.7699 |
| H(8A1) | 0.0433 | 0.8258 | 0.6487 |
| H(8A2) | 0.1532 | 0.7716 | 0.5395 |
| H(9A1) | 0.2021 | 0.9936 | 0.4892 |
| H(9A2) | 0.0755 | 1.0486 | 0.5852 |
| H(10A) | 0.3817 | 1.0203 | 0.6230 |
| H(10B) | 0.2591 | 1.1230 | 0.6924 |
| H(11A) | 0.2009 | 0.9445 | 0.8300 |
| H(11B) | 0.3760 | 0.9093 | 0.8166 |
| H(1A) | 0.5527 | 0.6147 | 0.8969 |
| H(3A) | 0.8530 | 0.4894 | 0.5683 |
| H(2B) | 1.2137 | 0.4531 | 0.7536 |
| H(4B) | 1.1270 | 0.3127 | 1.1022 |
| H(5B) | 0.9262 | 0.2136 | 1.0313 |
| H(7B) | 0.8021 | 0.2266 | 0.7158 |
| H(8B1) | 0.8919 | −0.0032 | 0.7579 |
| H(8B2) | 0.8745 | 0.0117 | 0.9050 |
| H(9B1) | 0.6546 | −0.0305 | 0.7352 |
| H(9B2) | 0.6625 | −0.0798 | 0.8791 |
| H(10C) | 0.5169 | 0.1076 | 0.9258 |
| H(10D) | 0.5074 | 0.1558 | 0.7819 |
| H(11C) | 0.6850 | 0.2517 | 0.9621 |
| H(11D) | 0.6230 | 0.3353 | 0.8384 |
| H(1B) | 1.0685 | 0.3853 | 0.6046 |
| H(3B) | 1.3417 | 0.5025 | 0.9259 |

*Hydrogen atoms were included in the refinement but restrained to ride on the atom to which they are bonded.

The data generated by single crystal X-ray analysis allowed the calculation of an X-ray diffraction pattern (i.e. a calculated XPRD). The results of these calculations are depicted in FIG. 2. These calculations allowed the determination of characteristic peaks associated with the Form C polymorph. A characteristic peak is a peak that does not overlap with any peak appearing in a X-ray diffraction pattern of the Form A polymorph or the Form I polymorph of the monohydrate of 4-cyclopentyl resorcinol (defined supra). The characteristic peaks of the Form C polymorph, expressed in degrees 2θ (approximate) are located at 15.4, 20.4, 22.0, and 23.3. The presence of at least one of these characteristic peaks in a crystalline sample of anhydrous 4-cyclopentyl resorcinol, submitted to experimental X-ray diffraction at a temperature of 160K, is sufficient to confirm that the sample is the Form C polymorph. In a further embodiment, the presence of at least two, three, or four of these peaks in a crystalline sample of anhydrous 4-cyclopentyl resorcinol submitted to experimental X-ray diffraction is sufficient to confirm that the sample is the Form C polymorph. Any experimental X-ray diffraction should be carried out as described above, to minimize the impact that a preferred orientation may have on the pattern generated.

A review of FIG. 2 identifies that additional peaks may be present in any sample of the Form C polymorph. A listing of peaks identified in the calculated pattern, including the characteristic peaks identified above, is listed below in Table VI. The data presented in Table VI should only be used to assist in the interpretation of an experimental X-ray diffraction analysis carried out on a crystalline sample of anhydrous 4-cyclopentyl resorcinol. The data should not be used to conclude that a crystalline sample of anhydrous 4-cyclopentyl resorcinol is not the Form C polymorph due to the absence of one, or more, selected peaks.

Table VIII

| 2θ[1] |
|---|
| 9.3 |
| 12.6 |
| 12.7 |
| 14.9 |
| 15.4* |
| 16.2 |
| 16.5 |
| 20.2 |
| 20.4* |
| 20.7 |
| 21.2 |
| 21.5 |
| 22.0* |
| 23.3* |
| 23.9 |
| 25.6 |
| 26.9 |
| 28.0 |
| 28.2 |
| 28.5 |
| 28.9 |
| 32.8 |

*Characteristic peak
[1]All stated 2θ values are approximate

The Form C polymorph has also been examined by infrared absorption spectroscopy. The IR spectra for this polymorph is shown in FIG. 3. Selected IR bands were identified that are unique to the Form C polymorph (i.e., are not present in the Form A polymorph). Form C exhibits the following unique absorption bands ($\upsilon_{max}/cm^{-1}$): 931.8 w, and 749.1 s.

E) Method of Preparation

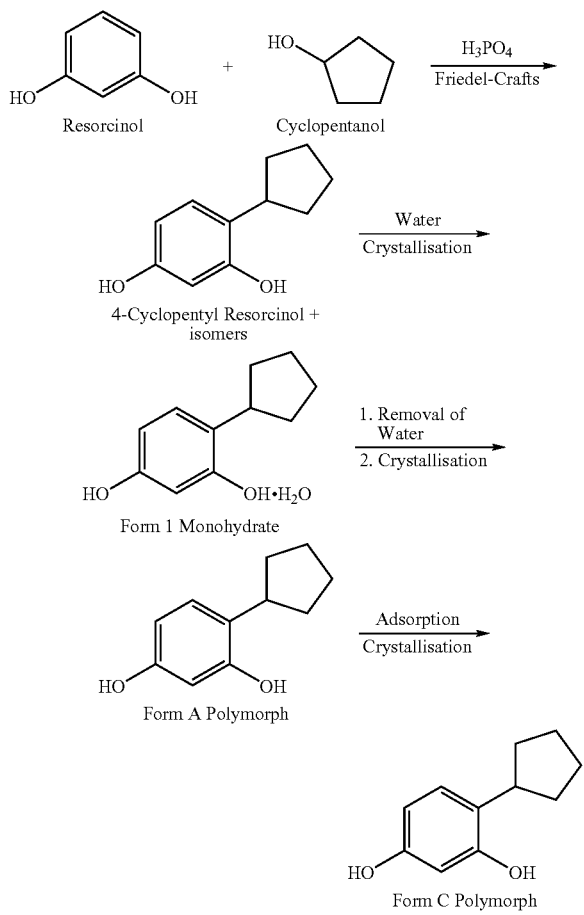

4-Cyclopentyl resorcinol, and its Form A and C polymorphs, may be prepared by methods analogously known to those skilled in the art, which are depicted in Reaction Scheme I.

The initial step is the preparation of 4-cyclopentyl resorcinol. This may be accomplished as described in U.S. Pat. No. 6,132,740, and U.S. Patent Application Ser. No. 60/446,665, both of which are hereby incorporated by reference. A Friedel-Crafts reaction is carried out in which resorcinol is reacted with an excess of cyclopentanol, in the presence of a catalyst such as polyphosphoric acid, and the admixture is heated until the reaction is completed. The 4-cyclopentyl resorcinol may be recovered by extraction. Evaporation of the organic phase of the extract generates an admixture of 4-cyclopentyl resorcinol and its positional isomers. The monohydrate form of 4-cyclopentyl resorcinol can be crystallized directly by addition of water and a suitable recrystallisation solvent such as toluene.

In order to obtain crystalline anhydrous 4-cyclopentyl resorcinol, it is necessary to modify the isolation and recovery procedures described above in the '665 application. A solution of the monohydrate is dried using an appropriate technique such as azeotropic distillation. The resulting anhydrous solution is concentrated and the resulting oil is dissolved in the recrystallization solvent, cooled, and the Form A polymorph is allowed to crystallise from solution. One suitable recrystallization solvent is an admixture of heptane and toluene. The ratio of toluene to heptane can vary widely. The Form A polymorph may be isolated by filtration, or evaporation, as is known in the art.

The Form C polymorph can be obtained by subjecting the Form A polymorph to a vapour adsorption crystallization using techniques analogously known in the art. The reader's attention is directed to Vogel's Handbook of Practical Organic Chemistry, A. I. Vogel, for a further discussion of such crystallizations. The Form A polymorph may be dissolved in a solvent such as toluene and an anti-solvent such as pentane at room temperature. The Form C polymorph will crystallize from this solvent admixture. The Form C polymorph may be recovered by evaporation or filtration as is known in the art. Other methods of producing the Form A and C polymorphs will become readily apparent to one skilled in the based upon the teachings of this application.

F) Pharmacology and Dose

As noted above, U.S. Pat. No. 6,132,740 describes the pharmacology of 4-cyclopentyl resorcinol. It is a tyrosinase inhibitor. It may be used to inhibit the production of melanin by melanocytes (i.e. inhibition of melanogenesis). The Form A and Form C polymorphs, are also tyrosinase inhibitors (hereinafter the "compounds"). They may be used in the same manner described in the '740 patent to inhibit melanogenesis. Thus, the compounds may be used to lighten areas of the skin that are inappropriately pigmented.

Examples of such inappropriate pigmentation include solar and simple lentigines (including age/liver spots), melasma/chloasma and postinflammatory hyperpigmentation. The compounds may also be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation.

The compounds may also be used in combination with sunscreens (UVA or UVB blockers) to prevent repigmentation, to protect against sun or UV-induced skin darkening or to enhance their ability to reduce skin melanin and their skin bleaching action. The compounds used in the present invention can also be used in combination with 4-hydroxyanisole. The compounds used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

As a general guideline the compounds will be administered topically. They will be applied directly to the areas of the skin requiring depigmentation, or lightening. Topical formulations such as creams, lotions, ointments, gels, etc. will be prepared which contain from about 0.1 to 10 w/w % of the compounds. The compounds will then be applied to the affected areas from 1 to 4 times daily. If the compounds are administered systemically, then from about 0.1 mg/kg to about 100 mg/kg will be administered daily, optionally as divided doses.

G) Pharmaceutical Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair (i.e. topical formulations).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

Typically however, the compounds will be incorporated into formulations suitable for topical administration. Any of the topical formulations known in the art may be used. Examples of such topical formulations include lotions, sprays, creams, ointments, salves, gels, etc. Actual methods for preparing topical formulations are known or apparent to those skilled in the art, and are described in detail in Remington's Pharmaceutical Sciences, 1990 (supra); and Pharmaceutical Dosage Forms and Drug Delivery Systems, 6th ed., Williams & Wilkins (1995).

In a further embodiment, the formulations described above may be packaged for retail distribution (i.e., a kit or article of manufacture). The package will contain instructions advising the patient how to use the product in order to lighten their skin. Such instructions may be printed on the box, may be a separate leaflet or printed on the side of the container holding the formulation, etc.

H) Examples

The following examples are presented in order to further illustrate the invention. They should not be construed as limiting the invention in any manner.

Example I

This Example illustrates one alternative method for the preparation of the Form A polymorph. A flask is charged with resorcinol (400 g, 3.63 mmol), cyclopentanol (312 g, 3.63 mmol) and phosphoric acid (85% in water, 1307 ml). The mixture is heated with nitrogen purge to 120° C. for 24 hrs. The solution is cooled to 100° C. and water (800 ml) is added. The solution is cooled to 60° C. and ethyl acetate (800 ml) is added. The solution is stirred for 10 minutes and transferred to a separating funnel. The aqueous layer is separated and is extracted with ethyl acetate (800 ml). The organic phases may be combined and washed with water (2×750 ml). The ethyl acetate is removed under vacuum at 40-50° C. to leave a purple oil.

The material is distilled under reduced pressure (1 mbar) at a pot temperature of 168 to 182° C. and vapour temperature of 164 to 166° C. Recrystallisation of the combined fractions (toluene-heptane) affords Anhydrate A.

Example II

A round bottom flask equipped with stirrer bar was charged with resorcinol (150 g, 1.36 moles), cyclopentanol (125 ml, 1.38 moles) and phosphoric acid (85% in water) 500 ml. The flask was fitted with a reflux condenser, purged with nitrogen and the mixture heated at 120° C. (oil bath temperature) for 26 h. After this time, TLC analysis indicated that starting resorcinol was still present. Further cyclopentanol (25 ml, 0.28 moles) was added to the reaction mixture and heating continued for 2.5 hours. On cooling, the mixture was diluted with water (500 ml) and ethyl acetate (600 ml). The organic layer was separated, and the aqueous layer extracted with ethyl acetate (3×500 ml). The combined organic layers were neutralized by careful addition of an excess of saturated aqueous sodium hydrogen carbonate solution, washed with brine (300 ml), dried (magnesium sulfate) and concentrated. The residue was dissolved in toluene (500 ml) and water (20 ml, 1.11 moles, 0.8 eq) added. The solution was stirred for ca. 30 s and cooled in an ice/water batch with periodic stirring. After 4 h the solid was filtered and left to air dry in a crystallizing dish for 16 h to give colored crystals. Recrystallization in toluene afforded the monohydrate form of 4-cyclopentylresorcinol as white plates. An anhydrous toluene solution of 4-cyclopentylresorcinol was prepared via azeotropic distillation. The solution was cooled, and pentane added. Anhydrate A was obtained by filtration. MPt 65-66.5° C. Selected IR Data ($v_{max}$/cm$^{-1}$): 1108.3 s, 1094.7 m, 977.8 s, 971.1 s, 930.4 w, 838.3 m, 826.7 s, 799.8 w, 748.1 w and 628.0 w.

Example III

This example illustrates one method for the preparation of the Form C polymorph. Anhydrate C was obtained via vapour adsorption crystallisation of Anhydrate A utilizing toluene (solvent) and pentane (anti-solvent) over a period of three days to yield the product as dendritic crystals, MPt 63.2-66.5° C. Selected IR Data ($v_{max}$/cm$^{-1}$): 1108.4 s, 977.9 s, 931.8 w, 826.8 s, 749.1 s and 628.0 m.

What is claimed is:

1. Form A polymorph of anhydrous 4-cyclopentyl resorcinol: a) which exhibits the following IR spectra absorption bands ($v_{max}$/cm$^{-1}$): 1094.7 m, 971.1 s, 930.4 w, 838.3 m, 799.8 w, and 748.1 w and b) that exhibits an experimental X-ray powder diffraction pattern, at temperature of 293 K, having characteristic peaks expressed in degrees 0 (approximate) at 18.7 and 19.7.

2. The polymorph of claim 1 which exhibits a single crystal X-ray crystallographic analysis at 293 K with crystal unit cell parameters that are approximately equal to the following:

| Space Group and Unit Cell Parameters | |
| --- | --- |
| Form | A |
| Crystal system | monoclinic |
| Space group | P2$_1$/c |

-continued

| Space Group and Unit Cell Parameters | |
|---|---|
| Cell Dimensions | |
| a(Å) | 9.582 ± 0.001 |
| b(Å) | 9.379 ± 0.001 |
| c(Å) | 11.076 ± 0.001 |
| β(°) | 97.405 ± 0.002 |
| Volume(Å$^3$) | 987 ± 1 |
| Z(Molecules/unit cell) | 4 |
| Density (g/cm$^3$) | 1.2 g/cm$^3$. |

3. The polymorph of claim 1 that exhibits an experimental x-ray powder diffraction pattern, at a temperature of 293K, having at least one characteristic peak expressed in degrees 2θ (approximate), selected from the group consisting of 13.3, 18.7, 19.7, 27.4, and 29.8.

4. A method for lightening skin comprising administering the Form A polymorph according to claim 1 to a patient in need thereof.

5. A method for reducing pigmentation in skin comprising administering the Form A polymorph according to claim 1 to a patient in need thereof.

* * * * *